Figure 1:
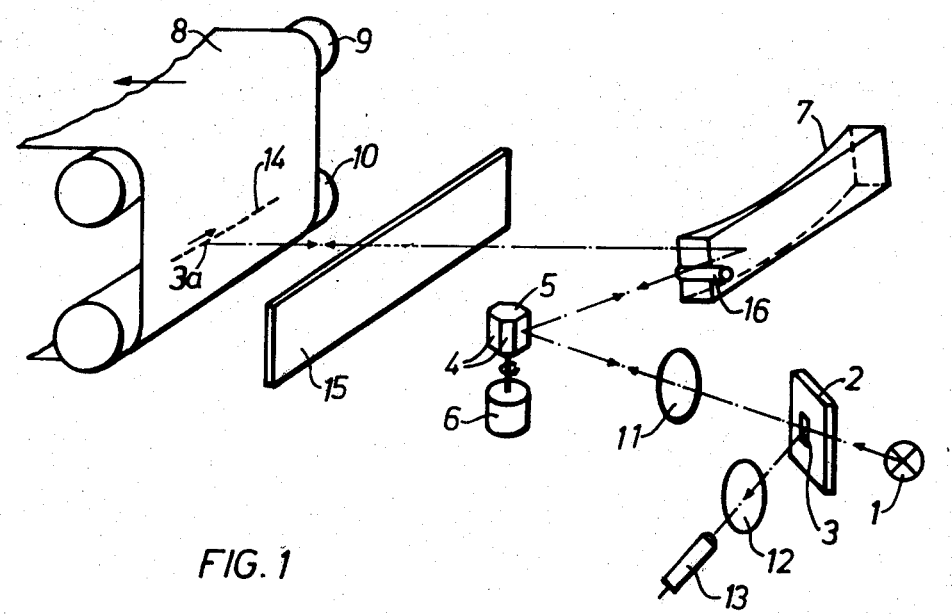

United States Patent [19]

Klein et al.

[11] 3,972,624
[45] Aug. 3, 1976

[54] PROCESS AND APPARATUS FOR DETECTING LONGITUDINAL FAULTS ON MOVING WEBS OF MATERIAL

[75] Inventors: Hans Joachim Klein, Wuppertal; Manfred Rupprecht; Heinz Wonneberg, both of Leverkusen; Julius Geiger, Odenthal-Gloebusch, all of Germany

[73] Assignee: AGFA-Gevaert, A.G., Leverkusen, Germany

[22] Filed: Dec. 11, 1974

[21] Appl. No.: 531,682

[30] Foreign Application Priority Data
Dec. 20, 1973 Germany............................ 2363422

[52] U.S. Cl................................ 356/200; 250/563; 250/572; 356/237
[51] Int. Cl.².......................................... G01N 21/32
[58] Field of Search ........... 356/199, 200, 202, 237, 356/238; 250/562, 563, 572

[56] References Cited
UNITED STATES PATENTS
| | | | |
|---|---|---|---|
| 3,510,664 | 5/1970 | Nichols................................ | 250/563 |
| 3,797,943 | 3/1974 | Nagao et al........................ | 356/200 |
| 3,812,373 | 5/1974 | Hosoe et al........................ | 356/200 |

Primary Examiner—John K. Corbin
Assistant Examiner—Richard A. Rosenberger
Attorney, Agent, or Firm—Connolly and Hutz

[57] ABSTRACT

In a process for detecting longitudinally orientated faults on moving webs of paper or film, the web is optically scanned line by line transversely to its direction of movement and read by reflection. The scanning line is moved to and fro across the whole web at constant velocity and during a given number of scanning movements the instantaneous value of the reflected signal is interrogated at two fixed time marks within the scanning line and stored and the average values over a scanning cycle are formed separately for each of the two time marks. The average values ae indicated and recorded as faults only if a value different from the average noise value is obtained from both time marks in succession.

13 Claims, 9 Drawing Figures

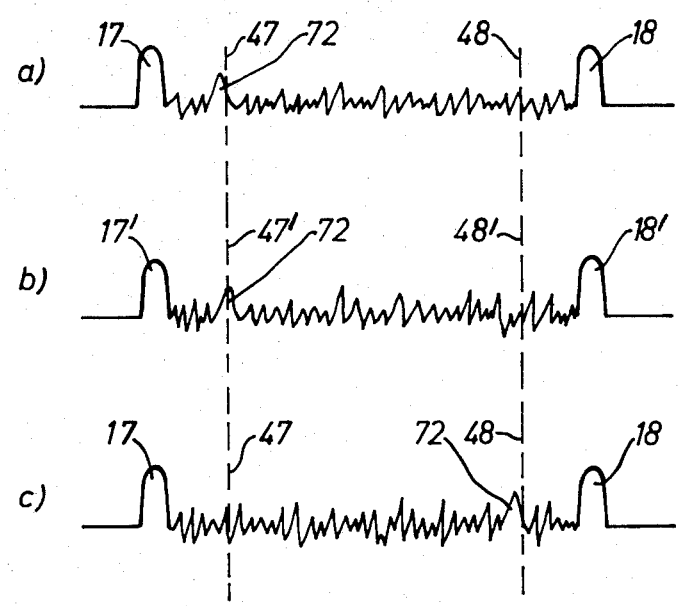
FIG. 4c
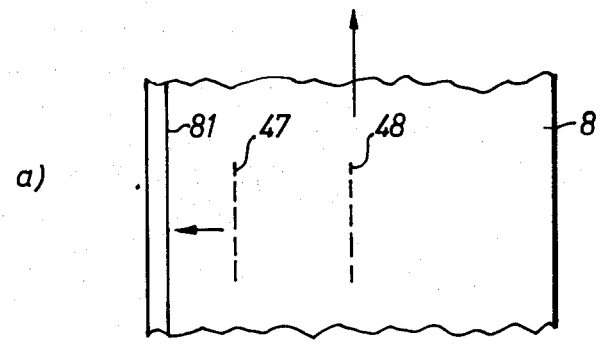
FIG. 5
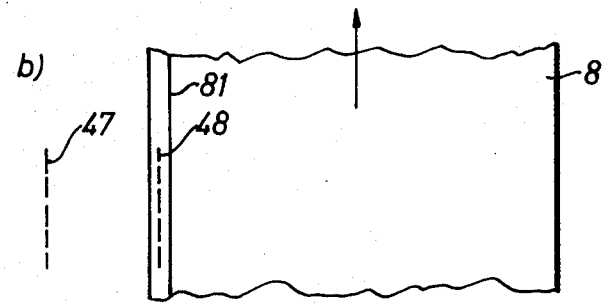

PROCESS AND APPARATUS FOR DETECTING LONGITUDINAL FAULTS ON MOVING WEBS OF MATERIAL

The invention relates to an optical process of and an apparatus for detecting, and recognising and localising longitudinally orientated faults on moving webs of paper or film, in particular on photographic materials. The web is scanned line by line transversely to its direction of movement and read by reflection.

In the manufacture of webs of material, in particular coated films such as photographic films and paper, faults may occur in the web, and particularly in the layers applied to the support, which may seriously impair the subsequent use of the web. Although punctiform faults such as specks of dirt, bubbles, etc. may occur it is faults extending in the longitudinal direction of the web, such as casting stripes or scratches, which may frequently extend over the whole length of the web, which are particularly likely substantially to reduce the quality. It is absolutely essential to detect such faults which extend longitudinally of the web.

Methods of detecting longitudinal faults are known in which the web is scanned optically by reflected or transmitted light of a suitable wavelength. This can be done, for example, by illuminating the moving web in uniform strips transversely to the longitudinal direction of the web and transmitting the reflected light (U.S. Pat. No. 3,206,606), or the transmitted light in the case of optically transparent webs (U.S. Pat. No. 3,286,567), to a photoelectric receiver or to a plurality of such receivers arranged side by side and parallel to the illuminated strip of web. To detect faults extending parallel to the longitudinal direction of the web, the detector arrangement may be reciprocated transversely to the longitudinal direction of the web. Intensity differences due to faults are perceived as light pulses by the photoelectric receivers and transmitted from the receivers to instruments for recording, controlling or storing the pulses.

In another process, a perforated band is moved transversely to the longitudinal direction of movement of the web and light is passed through the band so that the web is scanned in bands by the points of light produced by the perforations. The points of light passing through the web are then transmitted on the other side of the web to a plurality of photoelectric receivers or to a single detector by way of a photo-conductive rod (U.S. Pat. No. 3,331,963). Other scanning devices are known in which a patch of light is moved line by line transversely over the moving web by means of a rotating mirror, mirror wheel or similar optical element and the reflected light (e.g. U.S. Pat. Nos. 3,646,353 and 3,510,664) or the transmitted light in the case of optically transparent webs (U.S. Pat. No. 3,556,664) is passed through a lens system to be projected on to at least one photoelectric receiver.

In another process for detecting faults which extend parallel to the longitudinal direction of the web, the surface of the web is scanned by means of two fixed patches of light which are at a constant distance apart and staggered in line so that the light reflected from the web is transmitted to a separate photoelectric receiver for each of the two light patches and the whole scanning head is reciprocated across the width of the web transversely to the longitudinal direction of the web (German Offenlegungsschrift No. 1,573,801).

In another process which is employed especially for detecting longitudinal stripes (casting stripes) on photographic material in the moist state, the web is scanned by a reciprocating patch of light at the infrared absorption bond of water specifically to detect water (U.S. Pat. No. 3,564,265).

The methods described above for detecting faults on moving webs of material have one particular disadvantage. The light reflected or transmitted from the web and received by the photo-detector is modulated by the properties of the material of the web even where there are no faults since even a fault-free web is not normally completely uniform. The signal produced in the photo detector therefore has a certain irregularity (background noise) even in the absence of faults. In most cases where the methods described above are employed, the background noise is cut off electronically by an amplitude cut-off device such as a Schmitt-Trigger or a limiter diode, so that faults can be detected on the web of material only if the electrical pulse they produce is greater than the maximum interfering pulses and therefore greater than the discriminator voltage. Some improvement is obtained by a method in which a modified output signal of the photo detector is formed which is characteristic of the peak noise averaged over a time, and this output signal is compared with the original output signal of the photo-detector by means of a voltage comparator so that unwanted noise components are suppressed and the comparator yields an output signal only in the presence of a genuine fault pulse. In order to reduce the mistaken indications even further in faulty material the output signal of the comparator can in addition be transmitted to a discriminator with a constant threshold voltage (U.S. Pat. No. 3,510,664). Additional frequency-determining methods in the form of filters to separate pulses due to faults in the material from background noises (e.g. U.S. Pat. Nos. 3,510,664 and 3,206,606) do not provide a good solution since in practice there is usually hardly any difference in the frequency between pulses produced by faults and background noise. These arrangements serve merely to filter out unwanted interference frequencies which do not fall within the range of measured frequencies.

The detection of small faults, i.e. faults which give rise to pulses with an amplitude which is the same as or smaller than the noise amplitude cannot be achieved with the known methods mentioned above, but it is precisely the detection of such fine faults which is particularly important for the quality control of material webs, in particular of photographic material, if they are in the form of longitudinal faults often extending over whole length of the web.

It is an object of this invention to improve the optical detection of faults on moving webs of material to such an extent that even very fine longitudinal faults extending parallel to the direction of movement of the web of material, such as scratches or stripes, can be found with certainty. In particular, it is intended that such longitudinal faults on photographic materials should already be detected and recorded during the course of production. The fault detector arrangement according to the invention must therefore be so constructed that it can be installed directly behind a coating apparatus and that it can detect longitudinal faults while the web of material is still wet. Since point faults are often less significant in spoiling the quality of photographic materials than longitudinal faults, they should be eliminated by the instrument.

According to the invention, the problem is solved by means of an optical reflection scanner which scans the moving web line by line, the length of the scanning line being substantially smaller than the width of the web of material. The light which is reflected by the web and modulated by the surface properties of the web is transmitted to a photoelectric receiver fixed to the scanner. The process according to the invention is characterised in that a. the scanning line is reciprocated over the whole width of the web at a constant velocity, b. the instantaneous value of the reflected signal is interrogated periodically on two fixed time marks within the scanning line in the course of a given number of scanning operations (scanning cycle) and stored and the average values for each of the two time marks over a scanning cycle are formed separately, and c. the average values are indicated and recorded as faults only if a value different from the average noise value is supplied from both time marks in succession.

The instantaneous values interrogated at the two time marks are preferably stored as analogue values and then digitalised and the average value formed digitially for each time mark.

After expiry of such an operation for obtaining the average value during the given number of scanning movements, the average value formation begins again from the beginning for the next scanning cycle. While the scanning head traverses the width of the web, the two scanning marks also shift in the corresponding traversing direction. Where the web is free from faults, the statistically distributed background noise of the web which is due to the characteristic surface properties of the web is averaged out by the process while a longitudinal fault, even if fine, which produces a uniform positive or negative fault pulse during the scanning operation, will not fall within the average noise level but will produce a different value and will therefore be detected. In order to be recognised, the fault pulse must be detected successively in the correct sequence by each of the two time marks (scanning marks) which shift in the given traversing direction during the traverse motion. If the longitudinal fault is detected by the first time mark (scanning mark), the information of this fault is stored until the second time mark (scanning mark) has also passed across the fault. If the fault is recognised also by this second mark, then the information of detection of a fault is available for both time marks (scanning marks) simultaneously and the fault is recorded as a longitudinal fault. The minimum length of a fault which will still be detected as longitudinal fault therefore depends on the velocity of the traversing movement and the velocity of transport of the web of material. The lower the velocity of the web and the higher the velocity of traversing, the smaller will be the minimum length of a fault which will still be detected as a longitudinal fault. Faults in the form of points, which are often insignificant, are not detected by the process because the probability of the first time mark (scanning mark) falling on a point fault and the second time mark (scanning mark) also passing over a second point fault after expiry of the storage time is very slight.

The two time marks within the scanning line are preferably set by a line starting pulse.

In a preferred embodiment of the invention, the electrical output of the source of the beam (source of light) is regulated so that the intensity of the beam reflected from the surface of the web remains constant. The incoming or outgoing pulse appearing at the beginning or end of each scanning line is used to control this regulation.

The optical reflection system for carrying out the process according to the invention consists of a source of light, a mirror wheel with a focusing device (scanner) and a photoelectric detector arranged as an automatic collimating system, and an electronic processing circuit to process the signals supplied from the detector. The characteristic feature of this arrangement is that the scanner including the detector is mounted on a carriage which is movable transversely to the direction of the web so that the scanning line of the scanner traverses the moving web, and the electronic processing apparatus consists of a circuit which carries out quasi-continuous averaging of the signals from the detector.

The electronic processing circuit advantageously consists of the following units:

a. a sample and hold member suitable for positive and negative voltages which is switched to "hold" in the rhythm of the time marks for a period which is shorter than the time between two scanning marks and remains switched to "sample" for the rest of the time;

b. a voltage-frequency converter both for positive and for negative voltages, which converts the voltages at the output of the sample and hold member into a pulse sequence with a frequency proportional to the voltage and transmits the hold values during a conversion time lying within the hold time to two forwards-backwards counters connected into the circuit of the two time marks, in which counters the digital formation of the average value takes place and at the outputs of which counters a pulse is produced when, starting from a pre-adjusted value, an upper limit is exceeded in the case of forward counting or the value falls below the lower limit in the case of backward counting;

c. a digital control circuit controlled synchronously with the traversing device, in which the pulses at the output ends of the forward-backward counters are transmitted to the registering instrument only when a pulse is supplied successively from each of the two forward-backward counters, and only if the time sequence of these pulses corresponds to the sequence with which the two time marks successively detect a fault signal produced by one and the same fault in the course of their traversing movement.

The line starting pulse to set the two time marks is advantageously produced by means of a photoelectric diode installed in the scanner. The line starting pulse is subsequently amplified and standardised and transmitted to a monostable multivibrator which is triggered by it. Three other monostable multivibrators aare connected in series with this first multivibrator. The output of the first multivibrator and the output of the third multivibrator are connected to the control input of the sample and hold member by an OR gate. The effect of this circuit is that on transition from sample to hold function, one time mark is fixed by the first multivibrator and the following time mark by the third multivibrator. The voltage pulses by the two voltage frequency converters are transmitted to the next following forward-backward counters during a certain conversion time. The conversion time during which the voltage pulses produced by the voltage frequency converters are counted by the forward-backward counters is determined by the above mentioned multivibrators connected in series and an additional monostable multivibrator (fourth multi-vibrator). The second multivibrator produces the conversion time $T_2$ belong to one time mark and the fourth multivibrator produces the conversion time $T_4$ belonging to the following time mark.

The scanning cycle is preferably determined by the line starting pulse. For this purpose, the standardised line starting pulse controls a reducer in which the scanning cycle is fixed. In addition, after each scanning cycle, both forward-backward counters are reset to their preadjusted starting value by the previously converted output signal of the reducer.

The digital control circuit at the output end of the electronic processing circuit consists of two monostable multi-vibrators followed in series by an AND gate and an OR gate. The last two mentioned monostable multivibrators are unambiguously connected with the two traversing directions of the scanner so that there is always only one multivibrator ready in operation for the appropriate direction of traversing.

The voltage frequency converter is also preferably connected to the two time marks by the four gates and monostable multivibrators which are triggered by the line starting pulse.

In this arrangement, two gates are always switched off alternately when the time mark closest to the edge of the web in the direction of traversing leaves the surface of the web while the next following time mark still covers the surface of the web.

The advantages of the invention lie in the high degree of sensitivity with which faults in the form of stripes can be detected. The sensitivity is so high that even stripes which produce a reflection signal far below the noise level can be reliably detected. In addition, stripes can be clearly distinguished from point faults. The method used in the invention of forming the average value also ensures that the circuit is largely independent of external disturbances. Another major advantage is that the same apparatus can also be used for finding point faults. The reflection signals interrogated at the two time marks are then averaged in the same way but not logically linked together at the output of the electronic processing circuit as described above. Instead, the average values or only one of the two average values are registered directly. Even fast moving webs (2 meters per second) can be scanned without any gaps.

The structure and mode of operation of the invention will now be described in more detail with reference to an embodiment shown in the drawings.

Figure 2:
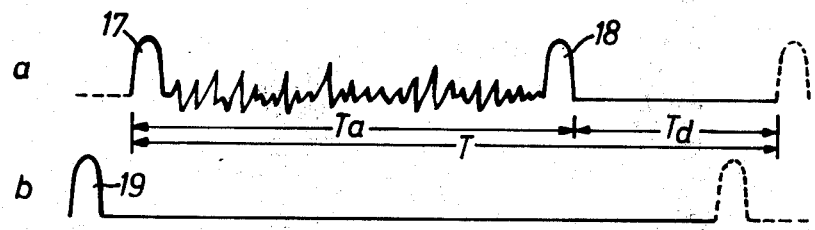
Figure 3:
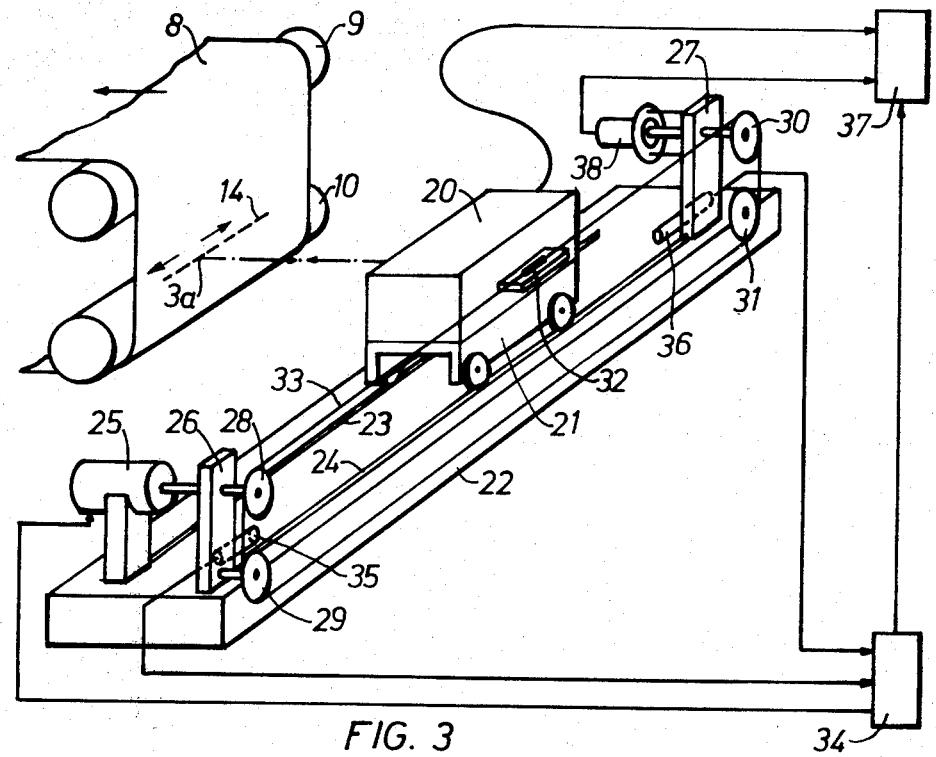
Figure 4A:
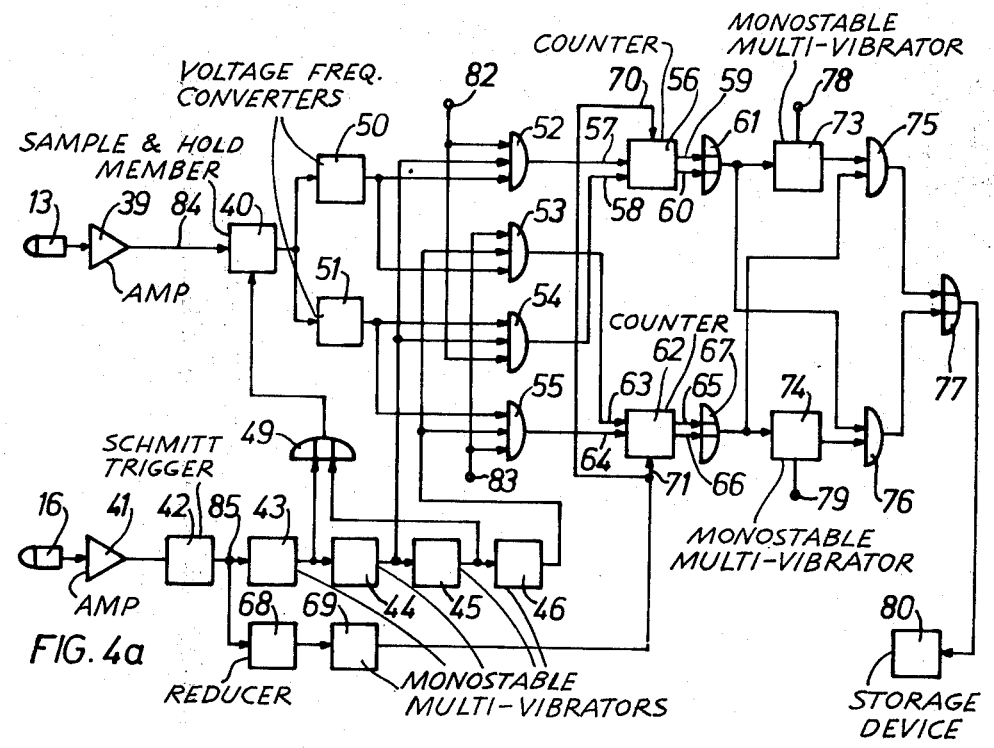
Figure 4B:
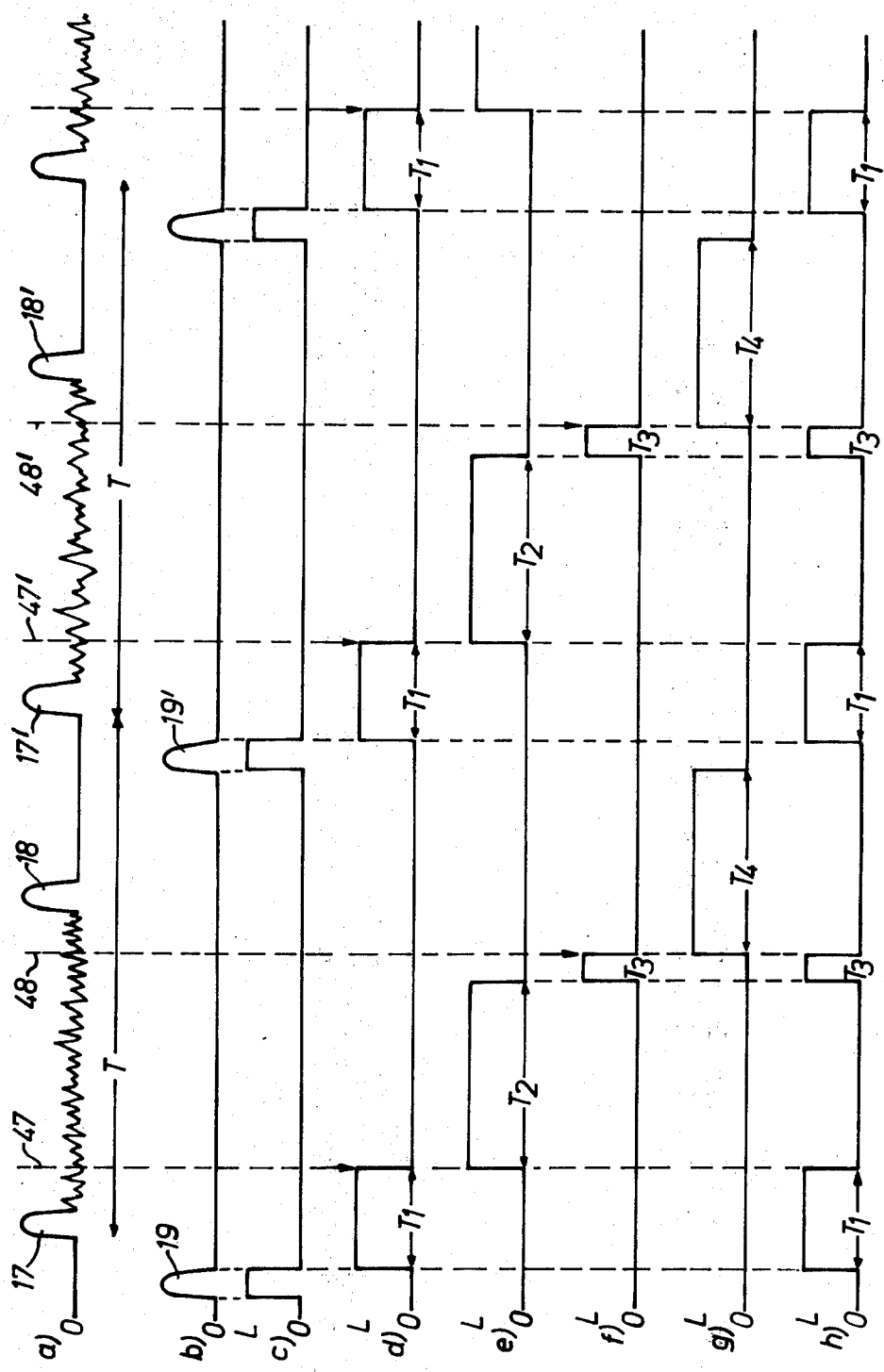
Figure 6A:
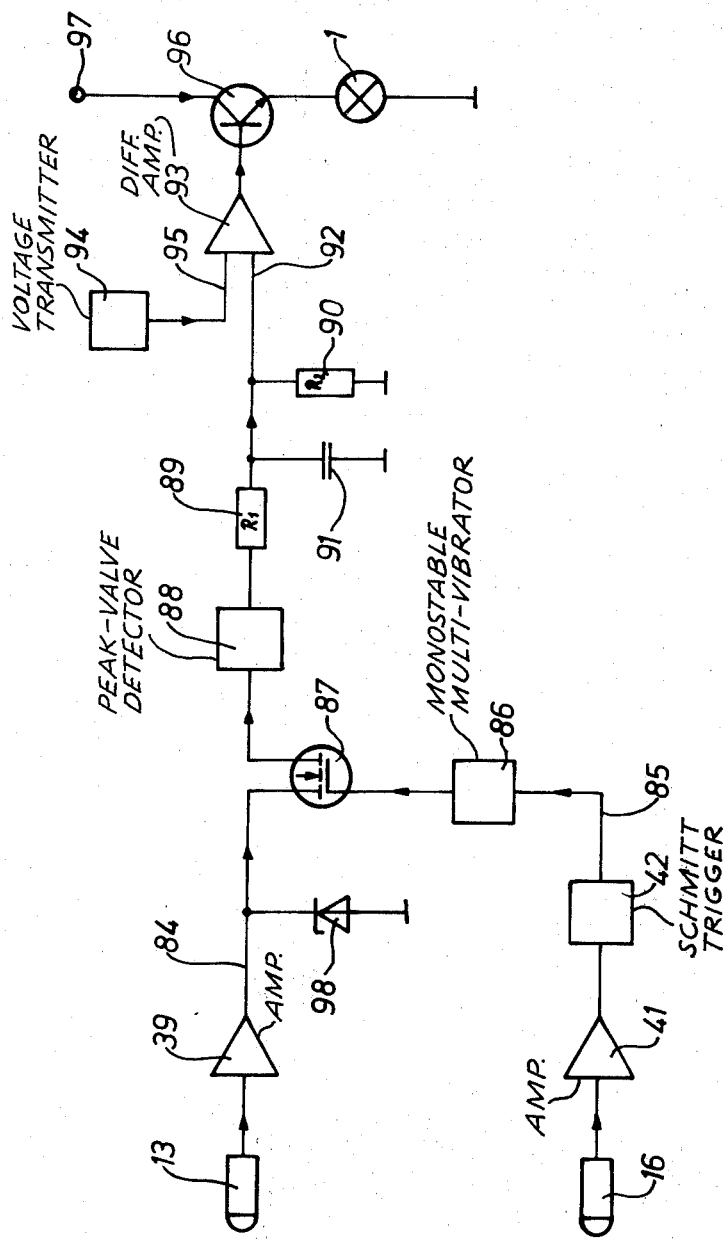
Figure 6B:
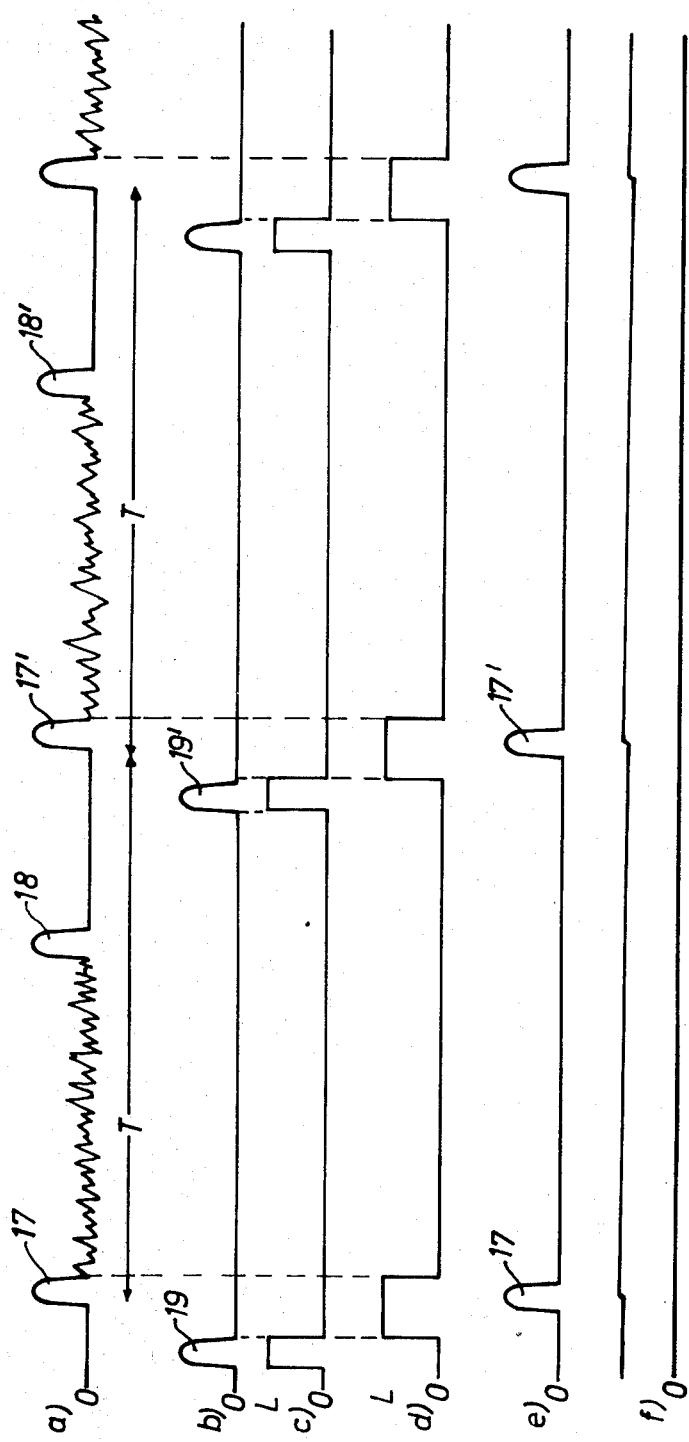

FIG. 1 shows schematically the arrangement of the optical reflection scanner,

FIG. 2 shows the signal for a line scanning received by the photoelectric receiver and the corresponding line starting pulse, FIG. 3 is a schematic view of the traversing arrangement, FIG. 4a a block circuit diagram of the electronic processing circuit, FIG. 4b is a pulse-time diagram corresponding to FIG. 4a for two successive line scannings of the optical scanner, FIG. 4c shows schematically the scanning of a longitudinal fault pulse at various times during the traversing movement, FIG. 5 shows schematically the recognition of longitudinal faults at the edge of the web, FIG. 6a is a block circuit diagram of the means for controlling the intensity of the light source, FIG. 6b is the pulse-time diagram corresponding to FIG. 6a.

FIG. 1 is a simplified view in perspective of an embodiment of an optical scanner. The scanner includes a source of light 1 which is a tungsten lamp. The light passes through a semi-transparent mirror 2 arranged at an angle of, for example, 45° to the incident light and through an inlet gap 3 which is adjustable in height and width and which is fixed to the back of the mirror 2.

A rotatable mirror wheel 5 covered with plane mirrors 4 is rotated by a motor 6 so that as the wheel rotates the mirrors 4 move in the focus of a parabolic mirro 7 which is arranged parallel to the web of material 8 which itself moves in the direction indicated by the arrow. To avoid irregularities in the movement of the web 8, the web passes over two rollers 9 and 10 which are placed close together and over which the web is wrapped with as large a looping angle as possible.

A convex lens 11 focuses the light from the gap 3 on to the mirrors 4 of the mirror wheel 5 which reflect the light on to the parabolic mirror surface 7 which in turn projects it as a small scanning spot 3a on to the web of material 8 with a direction of incidence perpendicular to the surface of the web. Since the mirror wheel is situated below the parabolic mirror 7, the wheel 5 and mirror 7 are set at a slight angle to each other for purposes of reflection and focusing. The light reflected by the web 8 and modulated by the surface properties of the web retraces its path to return to the semi-transparent mirror 2 by way of the parabolic mirror 7, mirrors 4 and lens 11. It is then deflected by the mirror 2 and focused by a convex lens 12 on to a photoelectric receiver 13 which may, for example, be a rapid, highly sensitive and as far as possible low-noise photoelectric diode or photo-transistor. The scanner thus operates on the principle of automatic collimation.

When the mirror wheel 5 rotates in the sense indicated, the beam reflected by the parabolic mirror 7 shifts parallel to itself in the direction indicated so that the scanning spot 3a scans the web 8 along the scanning line 14. The system is so arranged that only one mirror 4 of the mirror wheel 5 is used for each scanning operation. If the web 8 moves in the direction of the arrow, it is therefore scanned line by line without gaps along the length of the scanning line 14.

A fault on the web of material is detected by the scanning spot 3a and transmitted via the parabolic mirror 7, mirror wheel 5, lens 11, semi-transparent deflecting mirror 2 and lens 12 to the photoelectric detector 13 which converts it into an electrical fault pulse which is then processed in an electronic circuit, which will be described with reference to FIG. 4, where it is recognised and recorded.

When the system is used to check photographic material, an infrared filter 15 which absorbs light in the visible spectrum is arranged between the parabolic mirror 7 and web 8.

The entrance and exit of the scanning means at the ends of the parabolic mirror 7 produce pulses but these do not interfere with the process. On the contrary, they can be used to control the intensity automatically, as will be explained in more detail below.

Laterally to the parabolic mirror, another photoelectric diode 16 is arranged in the path of the beam of light so that it is swept by the beam and produces a line starting pulse before the beginning of each scanning operation. Other means could be used for producing this line starting pulse, e.g. inductive scanning of the mirror wheel.

By way of example consider the case where the scanning width is 7 cm, equal to the length of the scanning line 14, and the speed of rotation of the mirror wheel 5 is 50 revs. per sec. If the number of mirrors 4 is 16, the scanning frequency is 800 Hz and hence the whole operational time of one mirror 4, that is to say the sum of the actual scanning time $T_a$ on the web 8 and a certain dark time $T_d$ between two mirrors, which depends on the geometry and number of mirrors, is $T = 1.25$ ms. If the rate of movement of the web is 40 m/min, for example, the web 8 during this time (1.25 ms) moves forward by 0.83 mm. Since the length of the scanning spot 3a in this example is 2 mm, the line by line scanning of the web leaves no areas thereof unscanned. If the web moves at higher speeds, complete scanning without gaps can still be achieved, e.g. by increasing the speed of rotation of the mirror wheel 5 or by increasing the length of the scanning spot 3a.

FIG. 2a shows the signal received by the photoelectric receiver 13 when a line of fault-free web is scanned. The signal is then modulated only by the normal surface properties of the web. The web is scanned from left to right. 17 is therefore the entrance impulse which is dependent upon the surface of the web and 18 is the associated exit impulse. $T = 1.25$ ms is the total operational time of the mirror, which is composed of the scanning time $T_a$ and dark time $T_d$.

FIG. 2b shows the associated line starting pulse 19 situated before each line scanning and received by the photoelectric diode 16.

FIG. 3 is a simplified view in perspective of an example of a traversing arrangement. 20 represents the optical scanner shown in FIG. 1. The scanner 20 is fixed to a carriage 21 which is adapted to move backwards and forwards on rails 23 and 24 parallel to the surface of the web 8, the rails 23 and 24 being connected to a stable support 22. As the carriage moves backwards and forwards perpendicularly to the longitudinal direction of the web, the scanning line 14 is moved backwards and forwards across the width of the web in the directions indicated by the arrows and at the same time the scanner 20 scans the web 8 along the scanning line 14. The drive for the traverse motion is provided by a motor 25, drive sprockets 28, 29, 30 and 31 mounted in bearing blocks 26 and 27, and a sprocket belt 33 which moves over these sprockets and is fixed to the scanner 20 by the clamp 32. When the carriage 21 reaches an end position, it is automatically switched to move in the opposite direction by means of a motor control 34 which will not be described in detail here and two limit switches 35 and 36 which are fixed to the bearing blocks 26 and 27 and adjusted to the width of the web. The switches 35, 36 may, for example, be inductive approximation initiators. The motor control 34 contains a device which taps the voltage supply of the motor 25 and transmits a signal in the form of a direct voltage dependent upon the given direction of the traverse motion to the electronic processing unit 37 the operation of which will be described in more detail with reference to FIGS. 4a and 4b. To fix the position of the scanner 20 in relation to the width of the web during the traverse motion, a transmitter 38 is provided, e.g. in the form of a potentiometer or a digital rotation transmitter, which is connected to the sprocket 30 and the signal of which is used in the electronic circuit 37 to determine the coordinate on the width of the web of a longitudinal fault.

FIG. 4a shows the circuit diagram of the electronic processing circuit 37 (FIG. 3) and FIG. 4b is the associated pulse-time diagram for two successive line scannings of the scanner (FIGS. 1 and 2). To explain the operation of the electronic circuit more clearly, FIGS. 4a and 4b will be considered together. The signal produced by the photoelectric receiver 13 in response to the reflected beam of light which is modulated by the properties of the surface of the web is amplified in the amplifier 39 to form a wide band and enters the input of a sample and hold member 40 (e.g. type SHA 1A of Analogue Devices, USA) which is suitable both for positive and for negative input amplitudes. The signal obtained at the output end of the amplifier 39 is shown in FIG. 4b (a) for two successive scanning lines. 17 is the entrance pulse already mentioned above and 18 the exit pulse for the first scanning line, and 17' and 18' are the corresponding pulses for the following scanning. $T = 1.25$ ms is the total operational time of one mirror.

The line starting pulse produced by the photoelectric diode 16 before the beginning of each scanning line is amplified in the amplifier 41 and transformed into a positive rectangular pulse in the Schmitt Trigger 42. FIG. 4b shows the variation with time of the line starting impulse 19 or 19' for the following scanning, FIG. 4b (c) shows the rectangular pulse standardised from this line starting impulse at the output of the Schmitt-trigger 42. After the Schmitt-Trigger 42, four monostable multivibrators 43, 44, 45 and 46 are arranged in series. These multivibrators produce positive rectangular pulses, and starting from the standardised line starting pulse (FIG. 4b–c) they are triggered in each case by the negative flank of the preceding pulse. FIG. 4b, (d) – (g) show the variation of the time. FIG. 4b (d) represents the variation with time of the monostable multivibrator 43, FIG. 4b (e) represents that of the multivibrator 44, FIG. 4b (f) that of the multivibrator 45 and FIG. 4b (g) that of the multivibrator 46. The corresponding pulse times are as follows: $T_1 = 160$ μs, $T_2 = 500$ μs, $T_3 = 40$ μs and $T_4 = 500$ μs. $T_2$ should be equal to $T_4$. Two time marks for scanning, indicated by the reference numerals 47 and 48 or 47' and 48', indicated by the arrows, are determined by the negative flank (from L to O) of the pulse produced by the multivibrator 43 (FIG. 4b (d)) and by the negative flank of the pulse produced by the multivibrator 45 (FIG. 4b (f)). These time marks are situated approximately symmetrically in relation to the pulses 17 and 18 or 17' and 18'.

The outputs of the monostable multivibrators 43 and 45 are passed through the OR gate 49 to be brought together at the control input of the sample and hold member 40. The variation with time of the output of the OR gate 49 is calculated by adding the variations with time in FIGS. 4b (d) and 4b (f). The result is shown in FIG. 4b (h).

If the control input of the sample and hold member 40 is at L potential, that is to say during the times $T_1$ and $T_3$, then the function sample is switched on. If on the other hand it is at the O-potential, then the function hold is switched on. The circuit is therefore always switched from sample to hold at the time marks 47, 48 and 47', 48' and to sample at the O-L transitions. The function sample means that the input signal is always at the output of the sample and hold member while when the circuit is switched to hold the signal value which is obtained at the input at that moment is maintained as a fixed voltage value at the output during the hold time. The output of the sample and hold member 40 is connected to two voltage frequency converters 50 and 51, the converter 50 being suitable for positive input signals and the converter 51 being suitable for negative input signals. Their function is to convert the positive or negative value at the output of the sample and hold member 40 during an exactly specified conversion time within the hold time (of the sample and hold member 40) into a pulse sequence of specified rectangular pulses with a frequency proportional to the said value. The conversion ratio is 10 kHz/V (e.g. Type W10 - 10B, BPS Electrical GmbH, Hanover).

As will be described in more detail below, the conversion time for the instantaneous value fixed at the scanning mark 47 or 47' and stored in the sample and hold member 40 is $T_2 = 500$ μs, and for the scanning mark 48 or 48' it is also $T_4 = 500$ μs. The conversion times for the two scanning marks are therefore equal.

The output of the voltage frequency converter 50 for positive input values is connected to one input of each of the AND gates 52 and 53, and the voltage frequency converter 51 for negative input values is connected to one input of each of the AND gates 54 and 55. The output of the monostable multivibrator 44 is connected to the second input of each of the gates 52 and 54 so that these gates are energised only during the conversion time $T_2$. The gates 52 and 54 are thus associated with the left hand scanning mark 47 or 47'. Their outputs are connected to the inputs of the forward-backward counter 56 in such a way that the output of the gate 52 is connected to the forward input 57 and the output of the gate 54 is connected to the backward input 58 of the counter 56. The forward-backward counter 56 can be preadjusted to a selectable value, e.g. the number 32. Two outputs of the counter are also preselected, the output 59 e.g. with the number 64 and the output 60 with the number 0. This means that when pulses reach the input 57, they are counted "forwards" from the number 32 onwards. When the preselected number 64 is reached, a pulse appears at the output 59. This happens after exactly 32 input pulses. If, on the other hand, pulses reach the backward input 58, they are counted "backwards" from the preset number of 32 onwards until the number O is reached, again after 32 pulses, and a pulse appears at the output 60. The outputs 59 and 60 of the counter 56 are connected together through an OR gate 61. The output of the monostable multivibrator 46 is correspondingly connected to the second input of the AND gates 53 and 55 so that these gates are energised only during the conversion time $T_4$. The gates 53 and 55 are therefore associated with the right-hand scanning mark 48 or 48'. Their outputs are connected to the two inputs of a forward-backward counter 62, the output of the gate 53 being connected to a forward input 63 and the output of the gate 55 to a backward input 64 of the counter 62 which, like the counter 56, is preset to the number 32 and an output 65 of which corresponds to the preselected number 64 while an output 66 is preselected to 0. The function of the counter 62 corresponds to that of the counter 56. The outputs 65 and 66 are combined through the OR gate 67.

The output of the Schmitt-Trigger 42 which produces the standardised line starting pulse (see FIG. 4b (c)) is connected to a pulse reducer 68 which reduces the line starting pulses by a factor of 8 : 1. After every eighth scanning, a signal appears at the output of the reducer 68, from which signal the monostable multivibrator 69 produces a short rectangular pulse of about 40 μs which is transmitted to the two presetting inputs 70 and 71 of the counters 56 and 62. By this arrangement, the counters 56 and 62 are again preset to the number 32 after every eight line scannings. The operation of the arrangement so far described will now be explained with the aid of an example. A scanning mark will first be considered. When the counters 56 and 62 have been preset to 32 by the arrangement described above, the first of eight line scannings again begins.

It will be assumed that during the first line scanning the instantaneous signal value of the noise of the web at the scanning mark 47 is +0.4 Volt, for example. This value is at the output end of the sample and hold member 40 during the hold time, is converted into a pulse sequence in the voltage-frequency converter 50, and is counted into the forward input 57 of the counter 56 through the energised AND gate 52 during the conversion time $T_2 = 500$ μs. At the given conversion ratio of 10 kHz/Volt, this corresponds to a number of $10^4 \times 0.4 \times 5 \times 10^{-4} = 2$ pulses. The counter 56 therefore has the new value 32+2=34. It will be assumed that in the next, i.e. second line scanning, the instantaneous signal value at the (left) scanning mark 47' is −1.2 Volt, for example. This value is converted into a pulse sequence by the voltage-frequency converter 51 and also put into the backward input 58 of the counter 56 through the energised AND gate 54 during the conversion time $T_2 = 500$ μs so that $10^4 \times 1.2 \times 5 \times 10^{-4} = 6$ pulses are substracted (counted backwards) from the value 34 stored there, and the new counting value is now 34−6=28. This process is continued during the next 6 scannings (three to eight). After that, the counter is preset to the number 32 as described above.

Since as a result of the movement of the web and the traverse movement of the measuring head the line scannings extend every time over different regions of the web, the surface noise of the web represented in FIG. 4b (a) appears to be statistically distributed so that the process described above forms the digital average value for eight scannings of the surface noise of the web since neither the preselected number 64 is reached at the output 59 of the counter 56 nor the preselected number 0 at the output 60, in other words no pulse appears at the output of the OR gate 61.

The process is similar for the right-hand scanning mark 48 or 48', etc. since the arrangement is symmetrical. In this case the sample and hold member 40, voltage-frequency converter 50, 51, monostable multivibrator 46, gates 53 and 55, counter 62 and OR gate 67 come into operation.

In the event of a longitudinal fault, a uniform positive or negative pulse appears inside the statistically distributed noise of the web. During the traverse movement of the scanner, first one scanning mark and then the other passes over this pulse at the traversing velocity and the pulse is continuously scanned. This is represented by way of example in FIG. 4c, (a)−(c) which represents a positive fault impulse 72 and traversing movement of the scanner from right to left. In this Figure, therefore, the fault pulse 72 moves from left to right in relation to the scanner, i.e. in relation to the scanning marks 47, 47' and 48, 48'.

FIG. 4c (c) shows the first of the eight scannings which as described above, make up a scanning cycle takes place. The fault pulse 72 has just been covered by the scanning mark 47. In the next following scanning movement, represented in FIG. 4c (b), the scanning mark 47' covers the fault pulse 72 at another point since the fault pulse 72 has moved slightly to the right relatively to the scanning mark due to the traversing movement. This process is repeated during the following six scanning movements of the cycle so that the fault pulse 72 is scanned by the scanning mark altogether eight times, each time at a different point. The time required for this is $8.T = 8 \times 1.25$ ms $= 10$ ms. In this example, therefore, the fault pulse must persist for this length of time during the passage of the scanning mark. This will be the case even with narrow pulses since the traversing velocity is very slow, e.g. 1 mm/10 ms. Since longitudinal fault pulses are uniform pulses, in this example the fault pulse 72 is always positive, each scanning is accompanied by voltage frequency conversion in the voltage frequency converter 50 (FIG. 4a) so that when the first scanning mark passes over the fault, pulses are counted only through the forward input 57 of the counter 56 by way of the AND gate 52 which is energised by the monostable multivibrator 44. The fault pulse 72 is recognised as a fault if, starting from the preset counter content 32, a further 32 pulses have been counted in after eight scanning movements so that the preselected number 64 is reached and consequently a pulse appears at the output 59 of the counter 56 and therefore at the output of the OR gate 61. This happens when the average scanned pulse value during the eight scannings of the fault pulse 72 is just equal to +0.8 Volt because the number of pulses counted into the counters 56 when the conversion ratio of the voltage frequency converter 50 is 10 kHz/Volt, the conversion time $T_2 = 500$ $\mu$s and eight scanning movements are carried out is then $10^4 \times 0.8 \times 500 \times 10^{-6} \times 8 = 32$. It can easily be checked that even the ascending flank of a triangular pulse lasting 20 ms and having an amplitude of 1.6 Volt corresponds to an average scanned pulse value of 0.8 Volt for eight scannings.

The amplitude of the fault pulse 72 may well only be equal to or even be smaller than the amplitude values of the noise of the web since the noise has no influence on the recognition of a fault because its amplitudes are averaged out.

After another traverse movement, the fault pulse 72 reaches the second scanning mark 48 (FIG. 4c (c)) which also recognises it as a fault (by the same procedure) as already described above, and in this case (FIG. 4a) the sample and a hold member 40, the voltage frequency converter 50, the monostable multivibrator 46, the AND gate 53, the counter 62 and the OR gate 67 come into operation in a corresponding manner.

The recognition of negative longitudinal fault pulses takes place in an analogous manner. In this case, the voltage frequency converter 51 and the AND gates 54 and 55 which are connected to the backward counting inputs 58 and 64 of the counters 56 and 62, in which the numbers are substracted from the preset number 32, come into operation. When the preselected number 0 is reached, a pulse appears at the outputs 60 (for the left scanning mark) or 66 (for the right-hand scanning mark)) and hence at the outputs of the OR gates 61 and 67.

To ensure that only longitudinal faults and no point faults are recognised, a given fault must be detected by both scanning marks during the traversing movement. The logical decision that the marks are dealing with one and the same fault is made in the circuit connected to the outputs of the OR gates 61 and 67. That circuit consists of two monostable multivibrators 73 and 74, AND gates 75 and 76 and an OR gate 77. The monostable multivibrators contain control inputs 78 and 79 to which a positive control voltage must be applied to release the multivibrator.

So long as such a voltage is not supplied, the multivibrator is blocked. This control voltage is tapped from the motor control 34 (FIG. 3) provided for the traverse movement, that is to say for a traverse movement from right to left a control voltage is supplied only to the control input 78 so that the monostable multivibrator 73 is released while the monostable multivibrator 74 and hence also the gate 76 remain blocked. When the traverse movement is from left to right, the multivibrator 74 is released while the multivibrator 73 and hence the gate 75 remain blocked.

When the scanner traverses from right to left as in the previous example, a pulse appears at the output of the OR gate 61 if the left scanning mark recognises the fault. This pulse releases the monostable multivibrator 73 which therefore produces a pulse which keeps the AND gate 75 open until the right-hand scanning mark recognises the fault so that the pulse appearing at the output of the OR gate 67 is transmitted to the recording or storage device 80 by way of the open AND gate 75 and OR gate 77. This recording or storage device 80 may also contain some function associated with the width of the faulty web derived from the transmitter 38 (FIG. 3).

When the scanner traverses from left to right, recognition of the fault at the right-hand scanning mark energises the monostable multivibrator 74 since a pulse appears at the output of the OR gate 67. The pulse of the multivibrator 74 then keeps the AND gate 76 open until the left-hand scanning mark detects the fault so that the pulse appearing at the output of the OR gate 61 reaches the processing unit 80 by way of the open AND gate 76 and the OR gate 77.

The length of the pulses produced by the two multivibrators 73, 74 must be greater than the time taken for the fault to move relatively from one scanning mark to the other during the traverse movement. At a traversing velocity of 1m/10 ms, for example, and a distance between the scanning marks of 40 mm, this time is 400 ms and consequently it is sufficient for the multivibrator pulse to last 500 ms.

The minimum length at which a fault will still be recognised as longitudinal fault depends on the distance between the two scanning marks, the traversing velocity and the velocity of longitudinal movement of the web of material. Starting from a time of 400 ms for the relative movement of the fault from one scanning mark to the other, this length of fault is 400 mm if the web moves longitudinally at the rate of 60 m/min = 1 mm/ms, for example.

Two point faults could simulate a longitudinal fault pulse if one of the faults is recognised by one scanning mark and the other fault by the other but the likelihood of such a combination of faults is very slight, particularly since a longitudinal fault could be simulated only if this coincidence were repeated several times.

The method described above for recognising longitudinal faults also enables faults close to the edge of the web of material to be detected. This is illustrated diagrammatically in FIG. 5 for the left-hand edge of the web of material 8. The traversing movement is from right to left (FIG. 5a). The longitudinal fault is first recognised by the left scanning mark 47. Shortly before the mark reaches the left-hand edge of the web, the AND gates 52 and 54 which are associated with the left scanning mark are blocked by their common input 82 which is otherwise open (FIG. 4a). This blocking of the AND gates is due to a signal which is produced by the detecting element 38 for the width of the web (FIG. 3) and which places the input 82 at zero potential. The left-hand scanning mark 47 is then unable to recognise the edge of the web as a fault. When the right-hand scanning mark 48 has also recognised the fault 81, the traverse movement from right to left is terminated by the limit switch 35 (FIG. 3) at the moment when the scanning mark 48 has just reached the left-hand edge of the web but is still on the web (FIG. 5b). When the traverse movement from left to right then begins, the blocked gates 52 and 54 are released by the zero potential at the input 82 being switched off, but only when the left-hand scanning mark is again situated on the web 8, so that the fault 81 is unambiguously detected, first by the right-hand scanning mark 48 and then by the left-hand scanning mark 47.

Recognition of a fault at the right-hand edge of the web takes place in an analogous manner, the right-hand scanning mark 48 being in this case rendered inoperative by blockage of the AND gates 53 and 54 by way of their common input 83 shortly before the scanning mark leaves the web. When the traverse movement is reversed, the blocking is removed as soon as the scanning mark 48 is again on the web 8.

The figures given to illustrate the example more clearly are purely arbitrary. They can be replaced by any other figures adapted to the problem.

In order to form the average value described above, it is advantageous always to start with approximately the same amplitude values of the web surface noise regardless of the particular web of material being examined so that once the values for amplification, counter presetting, counter preselection, etc. have been adjusted, they need not be reset each time the apparatus is used to investigate a new material or a material in which the surface properties alter in the course of the examination. For this purpose, the intensity of the scanning lamp 1 (FIG. 1) is automatically adjusted so that the surface noise signal transmitted to the photoelectric receiver 13 (FIG. 1) remains constant. This is illustrated in FIGS. 6a and 6b.

FIG. 6a shows the circuit diagram of the control circuit for the lamp intensity, 6b is the corresponding pulse-time diagram for two successive scannings. The control circuit proper (FIG. 6a) is connected between the points 84 and 85 of FIG. 4a. For the sake of completeness and clarity, the photoelectric receivers 13 and 16, amplifiers 39 and 41 and Schmitt-Trigger 42 have been shown again in FIG. 6a. In the pulse diagram FIG. 6b, the diagrams a, b and c are identical with diagrams a, b and c of FIG. 4b. FIG. 6b (a) therefore shows the output signal of the photoelectric receiver 13 amplified in the amplifier 39, comprising the incoming pulse 17 and outgoing pulse 18 or the pulses 17' and 18' for the following scanning. FIG. 6b (b) shows the variation with time of the line starting pulse 19 or 19' for the following scanning and FIG. 6b and (c) shows the standardised rectangular pulse obtained therefrom at the output of the Schmitt-Trigger 42.

The monostable multivibrator 86 is connected to the output of the Schmitt-Trigger 42. Its own output is connected to the gate of a field effect transistor 87 (self-blocking n-channel FET). Triggered by the negative rear flank of the Schmitt-Trigger pulse (FIG. 6b (c)), the monostable multi-vibrator 86 delivers a positive rectangular pulse (FIG. 6b (d)). For the duration of this pulse, the field effect transistor 87 which is normally blocked becomes energised. The pulse duration is selected so that only the incoming pulse 17 (or 17'), whose amplitude is a measure of the intensity of the light beam reflected by the web of material, can pass through the field effect transistor 87. FIG. 6b (e) shows the corresponding pulse diagram at the output of the field effect transistor 87. The incoming pulses pass from the output of the field effect transistor 87 to a peak value detector 88 e.g. (Type APM 1, Loetscher Elektronik) the output of which is connected to an input 92 (actual value input) of a difference amplifier 93 by way of the voltage divider which consists of the resistances 89 and 90 and a capacitance 91 which is connected in parallel with the resistance 90. A voltage transmitter 94 feeds a fixed positive direct voltage as a reference value to a second input 95 (reference value input) of the difference amplifier 93. The output of the difference amplifier 93 is connected to the base of an npn output control transistor 96 which is connected in series with the scanning lamp 1 and which has the lamp supply voltage fed into it at the collector.

The peak value detector 88 has the function of recognising the maximum of the incoming pulse 17 or 17' for each scanning and storing it analogously. The loading time of the peak value detector should be short compared with the scanning time T while the unloading time is such that the stored peak value can drop by about 1 percent per scanning so that a direct voltage corresponding to the peak value is available at the output of the peak value detector 88 as a measure of the intensity of the beam of light reflected by the web. The output signal of the peak value detector 88 is represented in FIG. 6b (f).

Additional smoothing of this signal is effected by the RC member 89, 91. Where a transition from higher to lower voltage values occurs due to the high resistance of the amplifier input 92, the resistance 90 serves for more rapid discharge of the condenser 91, but $R_1C$ must be $R_2C$ (e.g. $R_1C = 1s$, $R_2C = 10 s$).

The voltage at the actual value input 92 of the difference amplifier 93 is therefore a positive direct voltage corresponding to the intensity of the beam reflected by the web.

The control operation proceeds as follows. If the reflection properties of the web of material under investigation are reduced, for example due to a change of web, so that the intensity of the reflected beam and hence of the incoming pulse 17 are reduced, then the actual value direct voltage at the input 92 of the difference amplifier 93 also drops and consequently the difference between the fixed reference value voltage at the input 95 and the actual value voltage at the input 92 is increased. The output of the difference amplifier 93 therefore becomes more positive so that the npn output control transistor 96 is further energised and the intensity of the lamp 1 is increased. This process continues until the actual value reaches the reference value and hence the intensity of the reflected beam again reaches the original value.

Control in the reverse direction from higher to lower intensity takes place in an analogous manner.

To prevent the intensity control being affected by large interfering impulses such as may occur, for example, where parts of the web are glued, a Zener diode 98 is connected to the output of the amplifier 39 as an impulse cutting stage for large pulses. The Zener voltage is sufficiently high for the control not normally to be affected.

This automatically intensity control ensures that the intensity of the beam reflected by the web remains constant regardless of the reflection properties of the material under investigation so that the values which must be preadjusted for detecting a particular longitudinal fault, such as the amplification, presetting of the counter, preselection of the counter, etc. need only be adjusted once.

What we claim is:

1. A process for detecting and localising longitudinally orientated faults on moving webs, in which the web is scanned optically line by line trasversely to its direction of movement and read by reflection, wherein:
   a. the scanning line is reciprocated transversely over the whole web at a constant velocity,
   b. the instantaneous value of the reflected signal is interrogated periodically at two fixed time marks within the scanning line during a predetermined number of scannings which make up a scanning cycle and stored and the values obtained in the course of a scanning cycle are averaged separately for both time marks, and
   c. the average values are indicated and processed as faults only if a value deviating from the average noise value is supplied from both time marks.

2. A process according to claim 1, wherein the instantaneous values interrogated at the two time marks are stored as analogue values and then converted into digital form and the average value for each time mark is then formed digitally from these values.

3. A process according to claim 1, wherein the two time marks within the scanning line are determined by means of a line starting pulse.

4. A process according to claim 1, wherein the output of a source of light supplying the light for the optical scanning is so controlled that the intensity of the beam reflected from the surface of the web remains constant.

5. A process according to claim 4, wherein the incoming pulse or outgoing pulse appearing at the beginning or end of each scanning line is used to effect the said control.

6. An optical reflection arrangement for detecting and localising longitudinally oriented faults on moving webs comprising a source of light, a mirror wheel and, focusing device (together consituting a scanner) and a photo-electric detector in an automatic collimation arrangement, and an electronic processing circuit for processing signals delivered by the detector, wherein the scanner and detector are mounted on a carriage which is displaceable transversely to the direction of movement of the web so that the scanning line of the scanner traverses the moving web, and the electronic processing device comprises a circuit which carries out a quasi-continuous formation of the average value of the signals delivered by the detector.

7. An arrangement according to claim 6 wherein the digital control circuit comprises two monostable multivibrators with which an AND gate and an OR gate are connected in series, and two monostable multivibrators are connected into the circuit in such a way that they are unambiguously associated with the two directions of traversing so that at any given time only one of the last mentioned multivibrators is ready for operation, depending on the direction of traversing.

8. An arrangement according to claim 6, wherein the electronic processing device comprises:
   a. a sample and hold member adapted for both positive and negative voltages, which is switched in the rhythm of the time marks to "hold" for a length of time which is shorter than the time between the scanning marks and to "sample" for the rest of the time;
   b. two voltage frequency converters one for positive voltages and the other for negative voltages, each of which converters converts the voltage values at the output of the sample and hold member into a pulse sequence with a frequency proportional to the voltage and transmits the hold values to two forward-backward counters electrically connected to the time marks during a conversion period which lies within the holding time, in which counters the digital formation of the average value takes place and at the outputs of which a pulse is produced if, starting from a preset value, an upper limit is exceeded in the case of forward counting or the average value falls below a lower limit in the case of backward counting, and
   c. a digital control circuit which is controlled synchronously with the traversing device and in which the pulses appearing at the outputs of the forward and backward counters are transmitted to the recording instrument only if a pulse is delivered successively from each of the two forward-backward counters and the time sequence of these pulses corresponds to the sequence with which the two time marks successively cover a fault signal produced by one and the same fault in the course of a traverse movement.

9. An arrangement according to claim 8, wherein a line starting pulse is produced by a photoelectric diode and then amplified and standardised and then used to trigger a first monostable multivibrator which has second, third and fourth monostable multivibrators successively connected in series therewith the output of the first multivibrator and the output of the third multivibrator being connected to a control input of the sample and hold member by way of an OR gate, and at the changeover from the sample function to the hold function, one time mark being fixed by the first multivibrator and the following time mark being fixed by the third multivibrator.

10. An arrangement according to claim 9, wherein the conversion time during which the voltage pulses produced by the voltage frequency converters are counted by the forward-backward counters is fixed by the second and fourth monostable multivibrators the second multivibrator producing the conversion time belonging to one time mark and the fourth multivibrator producing the conversion time belonging to the following time mark.

11. An arrangement according to claim 9, wherein the standardised time starting pulse energises a reducer in which the scanning cycle is fixed and after each scanning cycle both forward-backward counters are returned to the preset starting value by the output signal of the reducer, which signal is converted in a monostable multivibrator.

12. An arrangement according to claim 9, wherein the two voltage frequency converters are associated with the two time marks by means of gates and the monostable multivibrators.

13. An arrangement according to claim 12, wherein the two of the gates are switched off at a respective input when that time mark which is closest to the edge of the web in the traversing direction leaves the surface of the web while the following time mark is still on the surface of the web.

* * * * *